(12) United States Patent
Awad et al.

(10) Patent No.: US 9,480,749 B1
(45) Date of Patent: Nov. 1, 2016

(54) METHOD OF PREPARING A NANOCOMPOSITE FILM INCLUDING STARCH NANOFIBERS

(71) Applicant: KING SAUD UNIVERSITY, Riyadh (SA)

(72) Inventors: Manal Ahmed Gasmelseed Awad, Riyadh (SA); Saba Ameen Al-Adeemy, Riyadh (SA); Taieb Aouak, Riyadh (SA); Awatif Ahmed Hendi, Riyadh (SA); Khalid Mustafa Osman Ortashi, Riyadh (SA); Waseem Sharaf Shamsan Saeed, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/877,908

(22) Filed: Oct. 7, 2015

(51) Int. Cl.
*A61K 47/36* (2006.01)
*A61K 31/616* (2006.01)
*C08B 30/10* (2006.01)
*A61K 9/70* (2006.01)

(52) U.S. Cl.
CPC ............ *A61K 47/36* (2013.01); *A61K 9/7007* (2013.01); *A61K 31/616* (2013.01); *C08B 30/10* (2013.01)

(58) Field of Classification Search
CPC ............................ A61K 9/7007; A61K 47/36
See application file for complete search history.

(56) References Cited

U.S. PATENT DOCUMENTS

| 6,709,526 B1* | 3/2004 | Bailey ................... A61L 15/28 127/29 |
| 2006/0083784 A1 | 4/2006 | Ignatious et al. |
| 2012/0021026 A1* | 1/2012 | Glenn, Jr. ............... A61K 9/70 424/401 |
| 2012/0048769 A1* | 3/2012 | Sivik .................... B29C 43/006 206/524.1 |

OTHER PUBLICATIONS

Huang et al., "A review on Polymer Nanofibers by Electrospinning and Their Applications in Nanocomposites," Composites Sci. and Tech., 2003, 63, pp. 2223-22253.

* cited by examiner

*Primary Examiner* — Michael B Pallay
(74) *Attorney, Agent, or Firm* — Richard C. Litman

(57) ABSTRACT

A method of synthesizing a nanocomposite film including starch nanofibers includes preparing nanofibers from starch, mixing the starch nanofibers with a drug to form a first mixture, adding water to the mixture to provide an aqueous solution, adding hydrochloric acid (HCl) and glycerol to the aqueous solution to provide a second mixture, maintaining the second mixture in a water bath, and drying the second mixture to form a nanocomposite film including starch nanofibers. The drug can be a drug including carboxylic groups. The drug can be acetyl salicylic acid (AsA). The film can be a nano starch/AsA composite film or nanocomposite film. The nanocomposite film can be used as a drug carrier and, thereby, improve drug delivery.

9 Claims, 9 Drawing Sheets

METHOD OF PREPARING A NANOCOMPOSITE FILM INCLUDING STARCH NANOFIBERS

BACKGROUND OF THE INVENTION

1. Field of the Invention

The present invention relates to nanotechnology, and particularly to synthesis of a starch/drug nanocomposite.

2. Description of the Related Art

There is a need to replace petroleum-based polymers used in pharmaceutical drugs due to the shortage of fossil resources and the impact of petroleum-based on the environment. Recently, researchers studied the potential of natural, renewable resources including starch, chitosan, chitin, and pectin in replacing non-degradable petroleum derivatives. Among all agricultural resources, starch is the most abundant food commodity. Starch contains more than two hydroxyl groups per anhydroglucose repeating unit, so that it can be combined with either a polyol or a cross-linking agent.

Thus, a method of synthesizing a nanocomposite including starch nanofibers solving the aforementioned problems is desired.

SUMMARY OF THE INVENTION

A method of synthesizing a nanocomposite film including starch nanofibers includes preparing nanofibers from starch, mixing the starch nanofibers with a drug to form a first mixture, adding water to the mixture to provide an aqueous solution, adding hydrochloric acid (HCl) and glycerol to the aqueous solution to provide a second mixture, maintaining the second mixture in a water bath, and drying the second mixture to form a nanocomposite film including starch nanofibers. The drug can be a drug including carboxylic groups. The drug can be acetyl salicylic acid (AsA). The film can be a nano starch/AsA composite film or nanocomposite film. The film can be a nano starch/AsA composite film or nanocomposite film. The nanocomposite film can be used as a drug carrier and, thereby, improve drug delivery.

These and other features of the present invention will become readily apparent upon further review of the following specification and drawings.

BRIEF DESCRIPTION OF THE D WINGS

Similar reference characters denote corresponding features consistently throughout the attached drawings.

DETAILED DESCRIPTION OF THE PREFERRED EMBODIMENTS

A method of synthesizing a nanocomposite film including starch nanofibers includes preparing nanofibers from starch to form starch nanofibers, mixing the starch nanofibers with a drug to form a first mixture, adding water to the mixture to provide an aqueous solution, adding hydrochloric acid (HCl) and glycerol to the aqueous solution to provide a second mixture, maintaining the second mixture in a water bath, and drying the second mixture to form a nanocomposite film including starch nanofibers. The second mixture can be maintained in the water bath for about twenty minutes at a temperature of about 90° C. The starch nanofibers can be prepared by dissolving starch in boiling water under vigorous stirring conditions to provide an aqueous starch solution, adding alcohol, e.g., ethanol to the aqueous starch solution to provide a mixture, and maintaining the mixture at a temperature of about 90° C. for about one hour. The starch nanofibers of the nanocomposite film including starch nanofibers can have a width of less than 5 microns. The drug can be a drug including carboxylic groups. The drug can be acetyl salicylic acid (AsA). The film can be a nano starch/AsA composite film or nanocomposite film. The nanocomposite film can be used as a drug carrier and, thereby, improve drug delivery.

Figure 1:
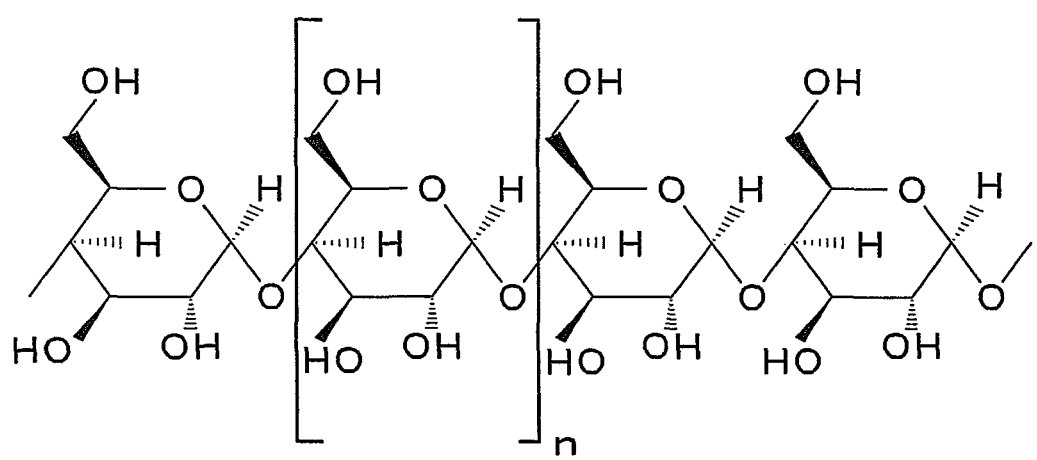
FIG. 1 shows the chemical structure of amylose.
Figure 2:
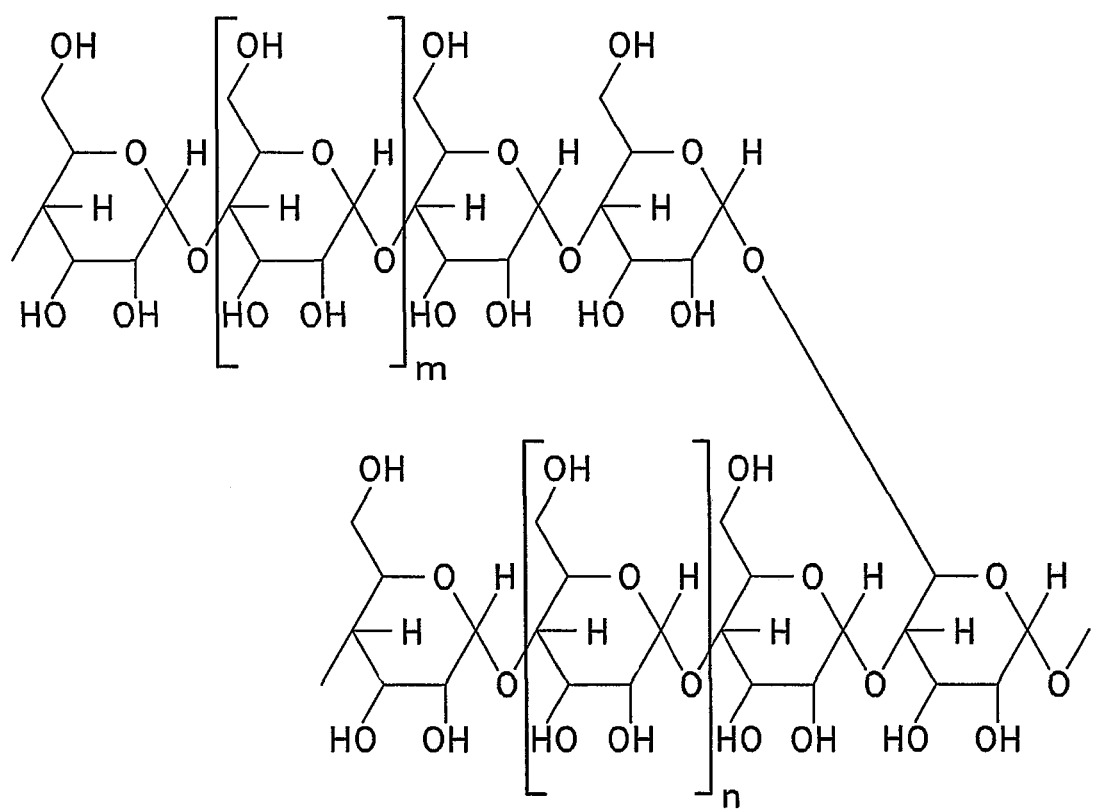
FIG. 2 shows the chemical structure of amylopectin.

As used herein, the term "nanofiber" refers to a fiber having a diameter of between about 1 and 100 nanometers. A "nanocomposite" is a multiphase solid material where at least one of the phases has one dimension of less than 100 nanometers (nm), e.g. between about 1 and 100 nanometers. As used herein the term"starch" or amylum is a carbohydrate consisting of a large number of glucose units $(C_6H_{10}O_5)_n$ joined by glycosidic bonds. This polysaccharide contains two types of molecules, 20 to 25 wt % of helical amylose (FIG. 1) and 75 to 80 wt % of branched amylopectin (FIG. 2) depending on the plant origin.

Using starch as a drug carrier is desirable because starch is renewable, non-toxic, low in cost, and is a bio-degradable polymer. However, the use of starch as a drug carrier has been limited in the past generally because of two factors, hydrophilicity and rapid enzymatic degradation. The present inventors have discovered that these problems can be avoided by blending starch with the active ingredient, as described herein. As explained in detail in the Examples below, use of the starch/AsA nano-composite film resulted in the increased release of AsA (more than 70 wt %) at pH 7 during a period of 76 hours. This result is found to be satisfactory and could be applied in a wide range of drugs containing carboxylic groups. The starch nanofibers and the composite of starch/drug nanofibers can be used as a coating and as a carrier for drugs.

It is believed that the starch nanofiber has an ability to respond to the different aqueous stomach mediums. For example, the starch nanofibers shrink in the acid medium so that the drug is protected from the effect of the acid of the stomach, yet expands in the intestinal medium (absorption medium) such that the drug is released. This effect is very surprising and extremely useful in controlling drug dosage.

Further, the starch nanofibers degradable gradually, which can facilitate predictable and consistent drug secretion for a long period of time.

Figure 3:
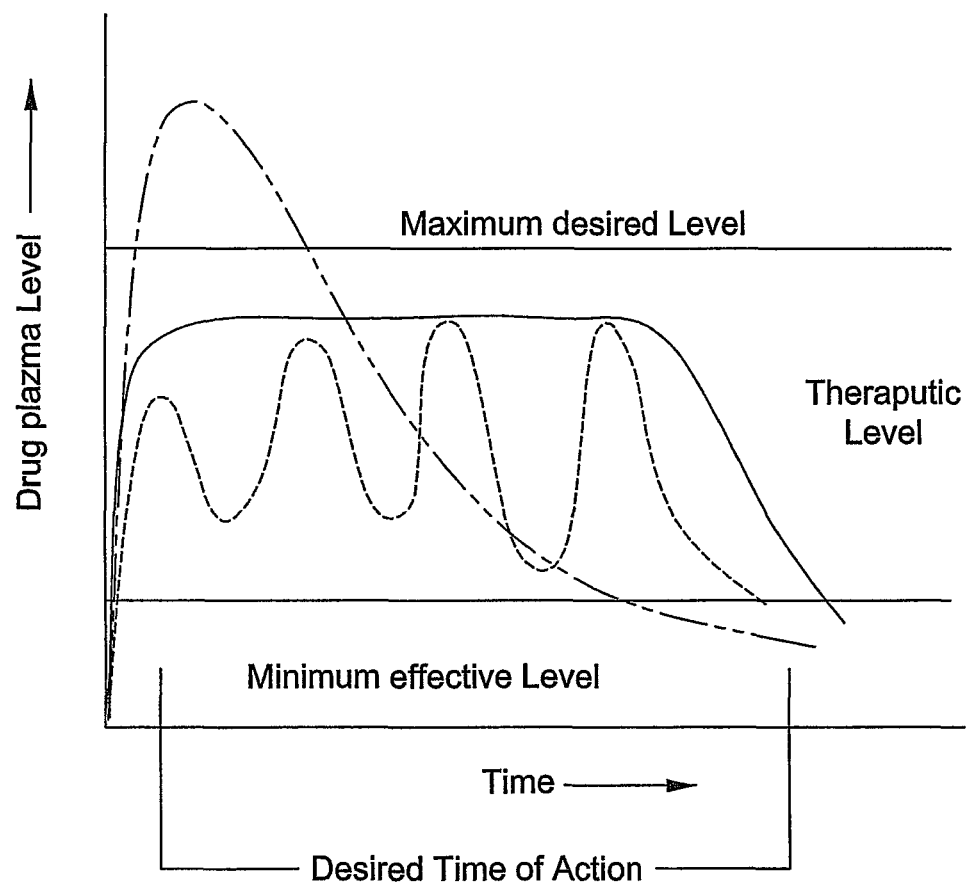
FIG. 3 shows a graph of the drug levels in the human blood.

The starch nanofibers are "green" or safe and environmentally benign. Further, the starch nanofibers provide medically effective techniques for controlling amount and frequency of release of drug doses in a patient. In many instances, controlled release of a drug is desirable. FIG. 3 shows a graph of drug levels in blood produced by various dosage forms.

The following examples will further illustrate the synthetic processes of making the starch nanofibers and the nanocomposite film.

Example 1

Preparation of Nanofiber of Starch

In a 100 ml beaker, 8.0 g of dry Starch was mixed with 100 ml of boiling water under vigorous stirring. Then, 30 ml of absolute ethanol was added to this aqueous solution. The resulting mixture was then kept at 90° C. for an hour.

Example 2

Preparation of AsA/Starch Nano-Composite Films

In a 100 ml beaker, 20 ml of nanofibers of dry starch was mixed with a known amount of Acetylsalicylic acid (AsA) (0.1 g) then 20 ml of distilled water. 3 ml of HCl (0.1N) and 2 ml of glycerol (50%) were added together to this aqueous solution. This mixture was kept at 90° C. in a water bath for 20 minutes then poured on a Teflon plate to dry at room temperature for 48 hours. The film was peeled off and washed several times with chloroform to remove the AsA residual (non-reacted).

Example 3

Characterization of the Starch-Nanofiber Composite

To confirm the structure of AsA/Starch nanocomposites, scanning electronic microscopy (SEM) was used to determine the surface morphology of the film before and after the release process. The transmission electronic microscopy (TEM) was used to determine the internal structure of the nanoparticles. The AsA released was controlled by UV-visible spectroscopy.

Figure 4:
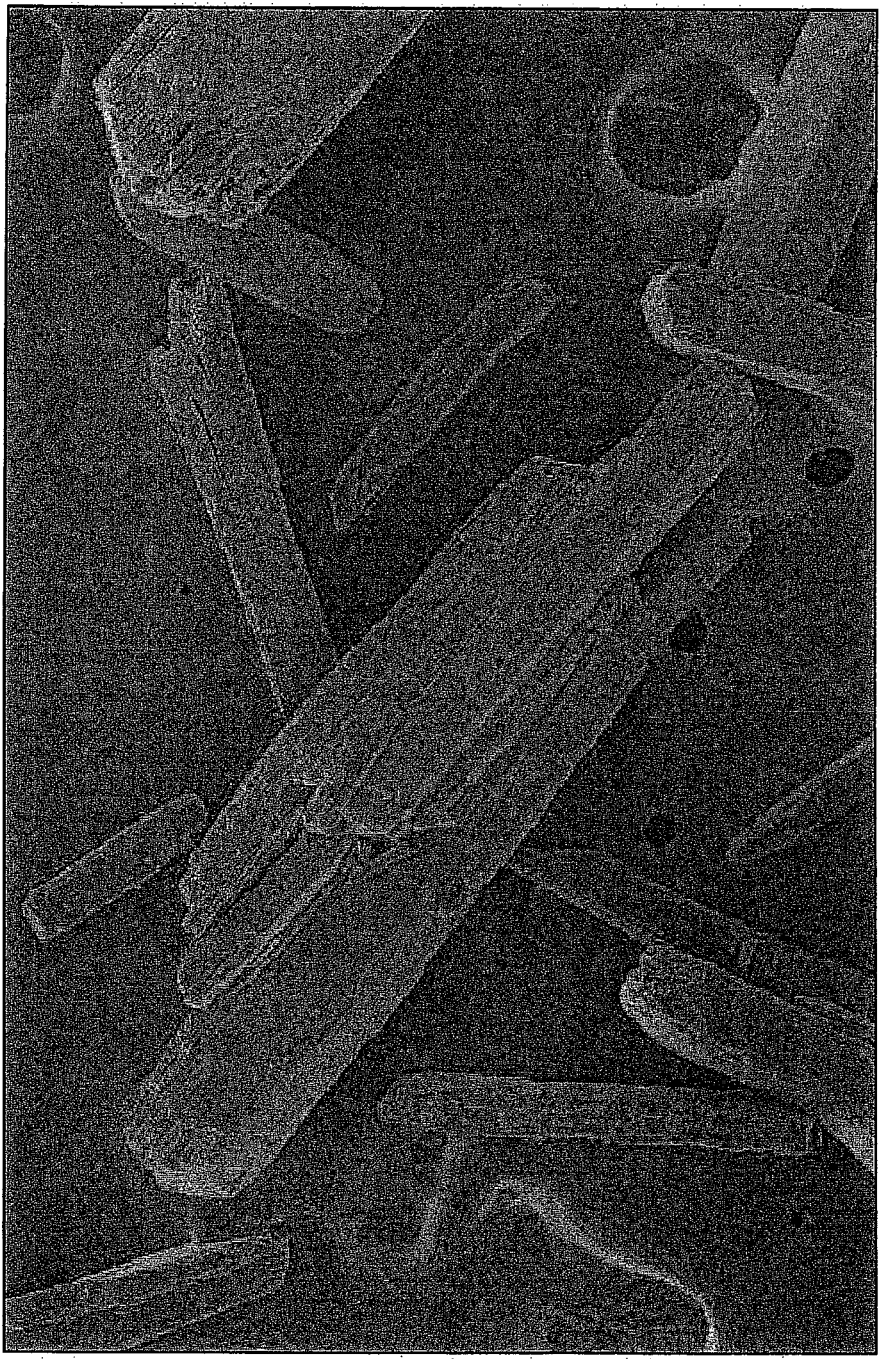
FIG. 4 shows the scanning electron micrograph (SEM) photomicrograph of acetylsalicylic acid (AsA).
Figure 5:
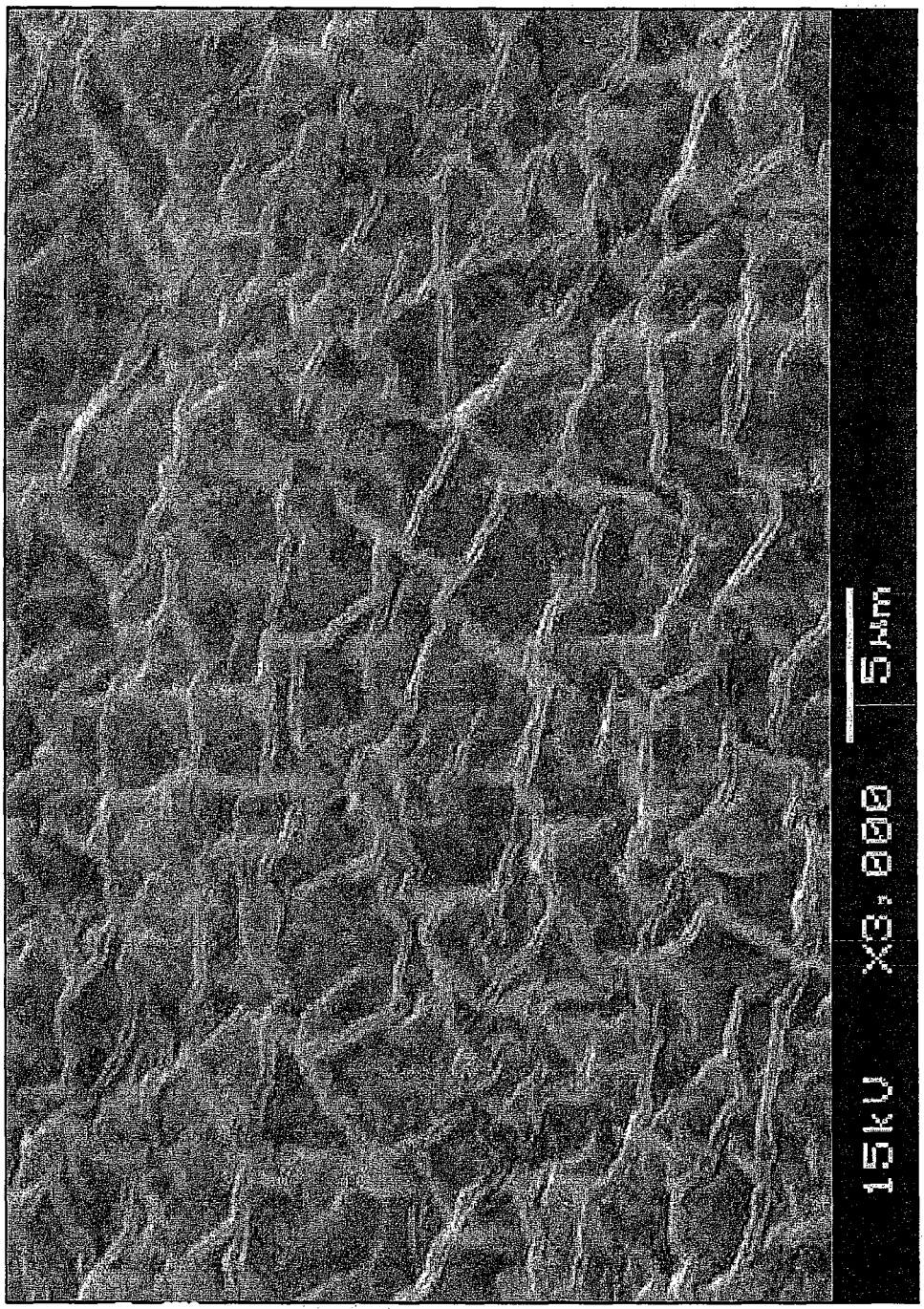
FIG. 5 shows the SEM photomicrograph of nano AsA/starch composite film before the AsA release process.

The surface morphology of nano-AsA/starch composite film was investigated by SEM. The SEM photography was considered the most intuitive method to exhibit the morphologies of surface features of nano-AsA/Starch composite before and after the release process. FIG. 4 represents the micrograph of pure AsA in which their particles have a typical crystalline paled in stick of wood form of different sizes gathered in aggregates of different sizes. FIG. 5 depicts the SEM micrograph showing the typical fibers of nano AsA/Starch composite film, which show that the nanofibers are distributed in the matrix and these fibers, have diameters less than 5 μm. The surface of the starch film as presented in this figure demonstrated no cracks, scratches or cavities.

Figure 6A:
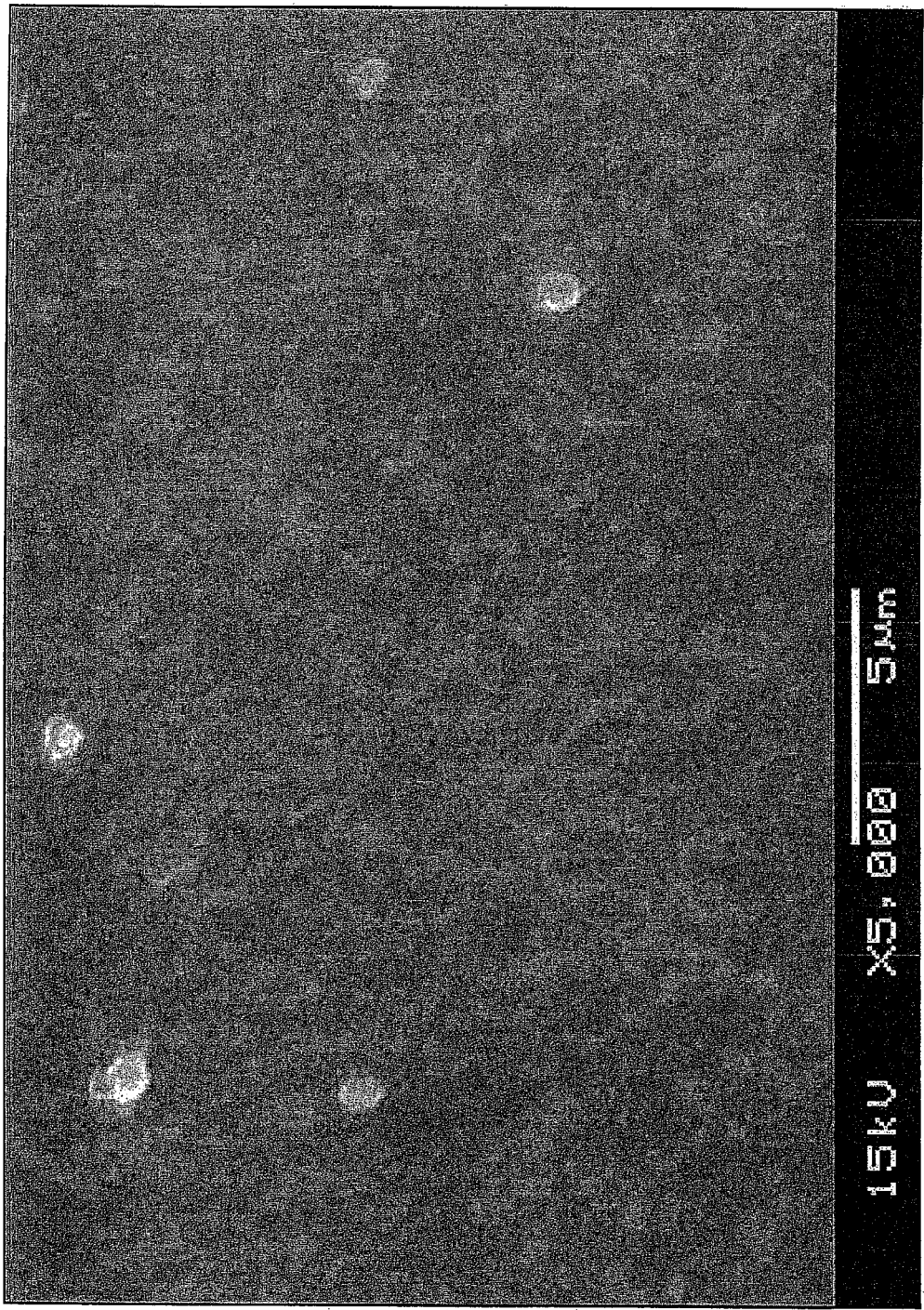
FIG. 6A shows the SEM photomicrograph of nano AsA/starch composite film after the release process at pH 1.
Figure 6B:
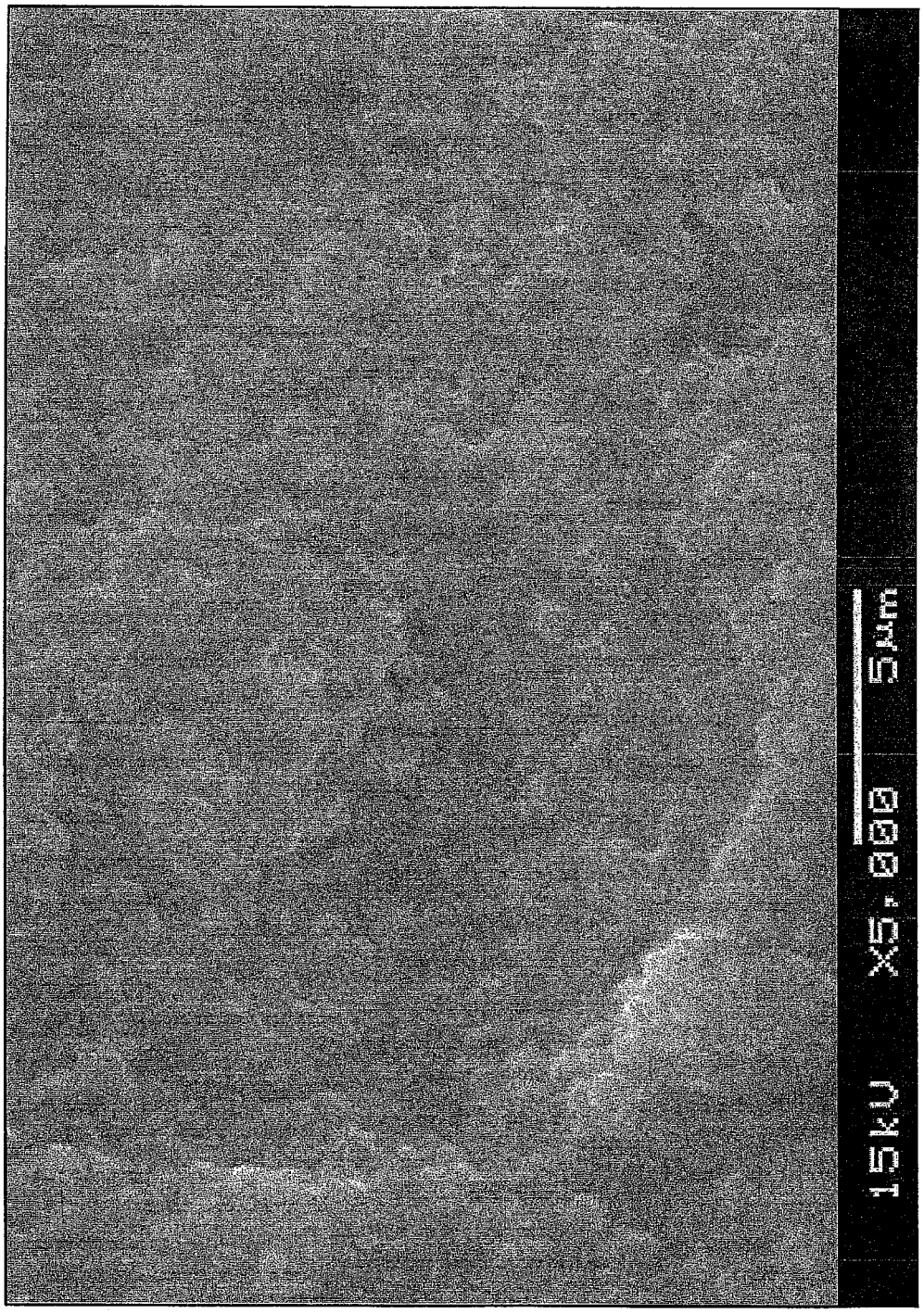
FIG. 6B shows the SEM photomicrograph of nano AsA/starch composite film after the release process at pH 7.

FIGS. 6A and 6B show the SEM micrographs of nano AsA/Starch composite film after the release process at pH 1 and pH 7 respectively. In both pH 1 and 7 the residue of AsA aggregates that were not released was observed on the surface, and was more marked when the pH of media was 7. Table 1 shows the variation of AsA released from nano AsA/starch composite versus time at different pH. The initial concentration was 1.96 wt % ($m_o$=7.843 mg, $m_r$ is the mass released at time T hours).

TABLE 1

| | pH | | | | | | | |
|---|---|---|---|---|---|---|---|---|
| | 1 | | 3 | | 5 | | 7 | |
| T (h) | $m_r$ (mg) | AsA released (wt %) | $m_r$ (mg) | AsA released (wt %) | $m_r$ (mg) | AsA released (wt %) | $m_r$ (mg) | AsA released (wt %) |
| 0 | 0.0 | 0 | 0.0 | 0 | 0.0 | 0 | 0.0 | 0 |
| 1 | 2.733 | 34.85 | 2.951 | 37.631 | 2.904 | 37.027 | 2.879 | 36.702 |
| 2 | 2.913 | 37.14 | 3.013 | 38.419 | 2.948 | 37.593 | 3.029 | 38.614 |
| 3 | 3.114 | 39.71 | 3.107 | 39.609 | 2.976 | 37.941 | 3.086 | 39.348 |
| 4 | 3.333 | 42.492 | 3.171 | 40.434 | 2.998 | 38.235 | 3.148 | 40.140 |
| 24 | 4.005 | 51.068 | 3.444 | 43.908 | 3.067 | 39.111 | 3.223 | 41.089 |
| 27 | 4.018 | 51.233 | 3.469 | 44.237 | 3.260 | 41.567 | 4.009 | 51.118 |
| 48 | 4.025 | 51.319 | 4.052 | 51.665 | 3.291 | 41.961 | 4.208 | 53.658 |
| 52 | 4.403 | 56.141 | 4.209 | 53.662 | 3.321 | 42.343 | 4.427 | 56.447 |
| 72 | 4.517 | 57.586 | 4.326 | 55.161 | 3.422 | 43.625 | 5.093 | 64.930 |
| 76 | 4.657 | 59.380 | 4.389 | 55.965 | 3.466 | 44.191 | 5.523 | 70.423 |

Example 5

General Observations of AsA Released from Nano AsA/Starch Composite Film

Figure 7:
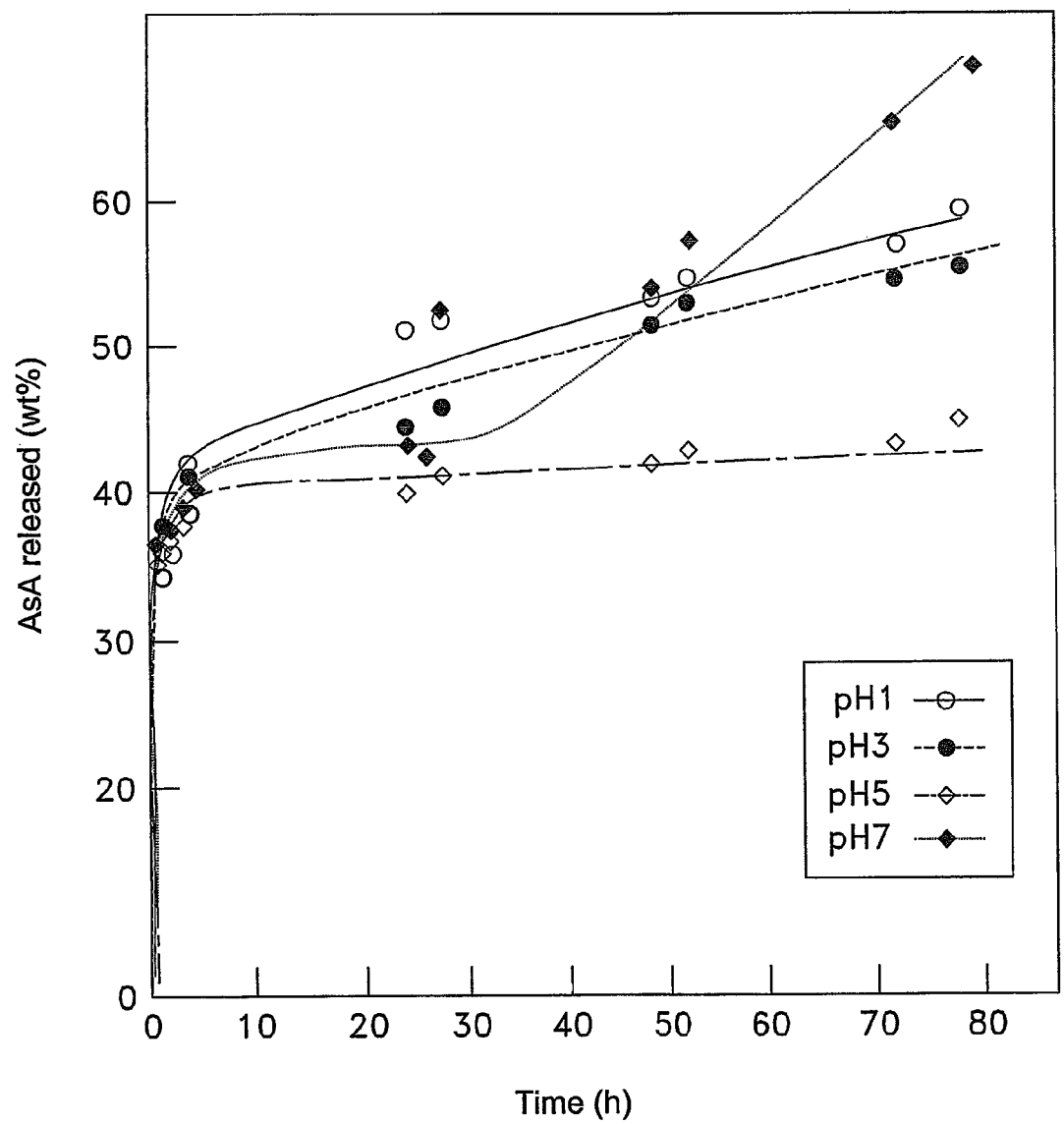
FIG. 7 shows the variation of AsA (wt. %) released from nano AsA/starch composite film versus time at various pHs.

The release dynamic of AsA from nano AsA/Starch composite film versus time is presented in Table 1. FIG. 7 presents the data graphically, showing the weight percent release at various pHs. According to the data obtained in this investigation, it was observed that the AsA amount released in acidic media from nano AsA/starch composite was characterized by two important zones. The first zone, observed during the first hours, indicated that the AsA released in the media increased dramatically with time. The second zone localized between 4 and 76 hrs. of the release process indicated that the release dynamic was very slow. The first zone is characterized by the high release dynamic probably due to the release of the AsA on the surface of nano AsA/starch composite film. The second zone is due to the release of AsA incorporated in the starch matrix. This zone is characterized by a pseudo-linearity of AsA released with time. At neutral pH, the composite containing 1.96 wt % of AsA show a positive deviation from linearity after 30 hours of the release process, thus creating a third zone. This abrupt deviation is due to a probable dislocation of nano AsA/Starch composite at neutral pH. In this case, a huge amount of AsA could be released in these conditions.

Example 6

Diffusion Behavior of AsA Through Nano AsA/Starch Composite Film

To understand diffusion behaviour, it is necessary to study the release dynamic of drug from the polymer matrix. To reach this goal, the Lin model was utilized in which the drug released from a polymer matrix must be inferior to 60 wt % of the initial drug amount incorporated in the polymer support. In this case, the release dynamic follows the Fickian model for diffusion from a polymeric film. The equation resulting from this model is given as Eq. (1):

$$\frac{M_t}{M_O} = k\sqrt{t} \tag{1}$$

Where $M_t/M_o$ is the fraction of drug released during (t) hours, k is a constant characteristic of each sample correlated to the release rate. The value of the diffusion coefficient, D, can be calculated according to the following relationship $$k = 4 \times \sqrt{\frac{D}{\pi \times l^2}} \tag{2}$$

Where l is the thickness of the film taken in this work as average thickness equal to 185 μm. The diffusion coefficient is calculated from equation (3) resulting from the combination of Eq. (1) and Eq. (2)

$$D = \frac{0.196 \times l^2}{t} \left[\frac{M_t}{M_O}\right]^2 \tag{3}$$

Figure 8:
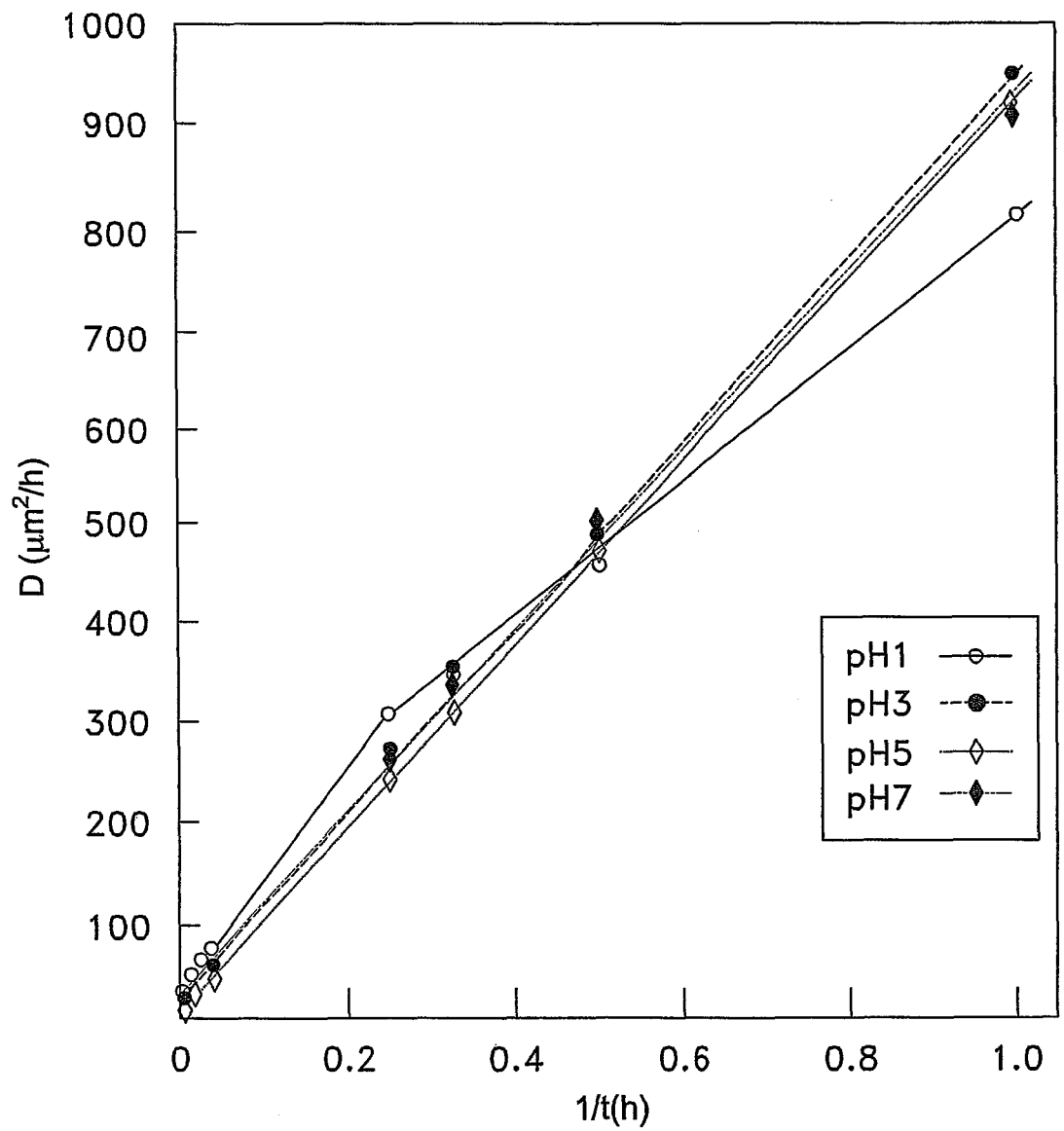
FIG. 8 shows the variation of the diffusion coefficient (D) of AsA from the nano AsA/starch composite film versus the inverse of time at different pHs and at 37° C.

The k and D values were determined when the permanent regime was reached and the AsA particles on the material surface were totally washed. In these conditions, the curves profile of D versus the inverse time has a meaning and reflects exactly the dynamic of AsA/water solution inside the material. FIG. 8 shows the variation of D versus the inverse of time calculated from the data of FIG. 7 using Eq (3) in the second zone. It was observed that the diffusion coefficient (D) linearly increased with 1/t. This finding perfectly confirms the Fickian model for diffusion from the nano AsA/Starch composite film. In light of this result, it was possible to build the investigation on the second zone of the release process in which the permanent regime was reached and the dynamic of the release was governed only by the diffusion phenomenon. Table 2 shows the diffusion coefficient of AsA diffused from nano AsA/Starch composite film versus the inverse of time at different pHs. The initial concentration was 1.96 wt %.

TABLE 2

| | | pH | | | | | | | |
|---|---|---|---|---|---|---|---|---|---|
| | | 1 | | 3 | | 5 | | 7 | |
| t (h) | 1/t (h$^{-1}$) | $\left(\frac{m_t}{m_o}\right)^2$ | D (μm$^2$/h) | $\left(\frac{m_t}{m_o}\right)^2$ | D (μm$^2$/h) | $\left(\frac{m_t}{m_o}\right)^2$ | D (μm$^2$/h) | $\left(\frac{m_t}{m_o}\right)^2$ | D (μm$^2$/h) |
| 1 | 1 | 0.121 | 811.68 | 0.142 | 952.55 | 0.137 | 919.66 | 0.135 | 905.59 |
| 2 | 0.5 | 0.138 | 462.86 | 0.147 | 493.05 | 0.141 | 472.92 | 0.149 | 499.75 |
| 3 | 0.33 | 0.158 | 349.76 | 0.157 | 347.55 | 0.144 | 318.77 | 0.155 | 343.12 |
| 4 | 0.25 | 0.181 | 303.54 | 0.163 | 273.36 | 0.146 | 244.85 | 0.161 | 270.00 |
| 24 | 0.042 | 0.261 | 73.53 | 0.193 | 54.38 | 0.153 | 43.11 | 0.169 | 47.57 |
| 27 | 0.037 | 0.262 | 65.03 | 0.196 | 48.65 | 0.173 | 42.94 | 0.261 | 64.78 |
| 48 | 0.021 | 0.263 | 37.05 | 0.267 | 37.61 | 0.176 | 24.79 | 0.288 | 40.57 |
| 52 | 0.019 | 0.315 | 40.15 | 0.288 | 36.71 | 0.179 | 22.82 | 0.318 | 40.53 |
| 72 | 0.014 | 0.332 | 31.18 | 0.304 | 28.55 | 0.190 | 17.84 | 0.422 | 39.63 |
| 76 | 0.013 | 0.353 | 30.78 | 0.313 | 27.30 | 0.195 | 17.03 | 0.496 | 43.25 |

It is to be understood that the present invention is not limited to the embodiments described above, but encompasses any and all embodiments within the scope of the following claims.

We claim:

1. A method of preparing a nanocomposite film including starch nanofibers comprising:
   providing an aqueous solution including starch nanofibers and a drug compound;
   adding hydrochloric acid (HCl) and glycerol to the aqueous solution to form a mixture,
   placing the mixture in a water bath; and
   drying the mixture to form a starch nanocomposite film.

2. The method of preparing a nanocomposite film including starch nanofibers according to claim 1, wherein drying the mixture comprises transferring the mixture to a plate and maintaining the mixture on the plate at room temperature for about 48 hours.

3. The method of preparing a nanocomposite film including starch nanofibers according to claim 1, wherein the water bath is maintained at about 90° C. and the aqueous solution is maintained in the water bath for about 20 minutes.

4. The method of preparing a nanocomposite film including starch nanofibers according to claim 1, wherein the starch nanofibers are prepared by dissolving starch in boiling water to provide an aqueous starch solution, adding ethanol to the aqueous starch solution to provide a mixture, and maintaining the mixture at a temperature of about 90° C. for about one hour.

5. The method of preparing a nanocomposite film including starch nanofibers according to claim 1, wherein the starch nanofibers in the nanocomposite film have a diameter of between about 1 and 100 nanometers.

6. The method of preparing a nanocomposite film including starch nanofibers according to claim 1, wherein the mixture is dried at room temperature for about 48 hours.

7. The method of preparing a nanocomposite film including starch nanofibers according to claim 1, wherein the drug includes one or more carboxylic groups.

8. The method of preparing a nanocomposite film including starch nanofibers according to claim 1, wherein the drug is acetyl salicylic acid (AsA).

9. A drug-starch nanocomposite film produced by the method of claim 1.

\* \* \* \* \*